(12) United States Patent
Broberg et al.

(10) Patent No.: US 6,280,195 B1
(45) Date of Patent: Aug. 28, 2001

(54) METHOD OF TREATING A PARTIALLY OR TOTALLY EDENTULOUS PATIENT

(75) Inventors: Leif Broberg, Mölndal; Anders Holmén, Hovås; Nils Gustaf Bergström, Vagnhärad, all of (SE)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 09/330,661

(22) Filed: Jun. 11, 1999

(51) Int. Cl.⁷ .................................................. A61C 8/00
(52) U.S. Cl. ............................................................. 433/201.1
(58) Field of Search ................................ 433/173, 201.1, 433/174

(56) References Cited

U.S. PATENT DOCUMENTS

| | | | |
|---|---|---|---|
| 4,180,910 | 1/1980 | Straumann et al. | 433/173 |
| 4,447,209 | 5/1984 | Sutter | 433/173 |
| 4,484,570 | 11/1984 | Sutter et al. | 128/92 |
| 4,758,161 * | 7/1988 | Niznick | 433/173 |
| 4,854,872 | 8/1989 | Detsch | 433/173 |
| 5,106,300 | 4/1992 | Voitik | 433/173 |
| 5,135,395 * | 8/1992 | Marlin | 433/174 |
| 5,196,016 | 3/1993 | Buser et al. | 606/72 |
| 5,306,149 | 4/1994 | Schmid et al. | 433/173 |
| 5,316,477 | 5/1994 | Calderon | 433/173 |
| 5,368,483 | 11/1994 | Sutter et al. | 433/173 |
| 5,417,568 * | 5/1995 | Giglio | 433/173 |
| 5,456,723 | 10/1995 | Steinemann et al. | 623/16 |
| 5,556,280 * | 9/1996 | Pelak | 433/173 |
| 5,688,123 * | 11/1997 | Meiers et al. | 433/173 |
| 5,779,480 * | 7/1998 | Groll et al. | 433/173 |
| 5,810,592 * | 9/1998 | Daftary | 433/173 |
| 5,908,298 * | 6/1999 | Durr et al. | 433/173 |
| 5,915,968 * | 6/1999 | Kirsh et al. | 433/173 |
| 5,989,029 * | 11/1999 | Ororio et al. | 433/173 |

FOREIGN PATENT DOCUMENTS

| | | |
|---|---|---|
| 684384 | 9/1994 | (CH) . |
| 0139253 | 5/1985 | (EP) . |
| 0388576 | 9/1990 | (EP) . |

* cited by examiner

*Primary Examiner*—Todd E. Manahan
(74) *Attorney, Agent, or Firm*—White & Case LLP (57) ABSTRACT

A method of treating a patient having a toothless site (10) in a jaw comprising the steps of providing a fixture (1) for anchorage in the bone (5) of the jaw at the toothless site having a coronal end (9); anchoring the fixture in the bone such that the coronal end is submerged beneath the coronal margin (8) of the gingival layer (7) at the toothless site; providing an abutment (31a; 31b; 31c) which is securable in an operational position to the fixture through an opening (12) provided through the gingival layer to the fixture, the abutment having a transgingival structure (37) which comprises an apical section (41) which tapers outwardly from an apical end of the transgingival structure which in the operational position of the abutment is co-planar with the coronal end of the fixture to a position at which the transgingival structure has a maximum transverse dimension and a coronal section (43) contiguous with the apical section which tapers inwardly from the maximum transverse dimension to a coronal end of the transgingival structure, the apical section terminating at the position of maximum transverse dimension with a convex outer surface profile; removing material from the transgingival structure so as to form a peripheral shoulder (54) of a profile which closely follows that of the coronal margin of the gingival layer at said opening; and forming a crown structure (60; 160) which seats on the peripheral shoulder when the abutment is secured to the fixture.

19 Claims, 8 Drawing Sheets

METHOD OF TREATING A PARTIALLY OR TOTALLY EDENTULOUS PATIENT

FIELD OF THE INVENTION

The present invention relates to a method of treating a patient having a toothless site in a jaw.

BACKGROUND OF THE INVENTION

The replacement of one or more lost natural teeth may be achieved by anchoring a dental implant to the jaw bone at the toothless site. A dental implant is typically defined by (i) one or more fixtures anchored in the jaw bone at the toothless site beneath the overlying gingival layer, the number of fixtures used depending on whether the dental implant is to be for a single-tooth replacement, in which case a single fixture is used, or for replacement of a number of lost teeth, in which case at least one fixture will be used (ordinarily a plurality of spaced-apart fixtures), and (ii) an abutment secured to each fixture through an opening provided in the gingival layer, the structure of the abutment which is disposed above the coronal end of the associated fixture projecting from the coronal margin of the gingival layer at the opening (hereinafter the "transgingival structure"). A structure which presents one or more artificial crowns (hereinafter a "crown structure") is then connected to the abutment(s).

Abutments in the main are presently prefabricated as standardised ready-to-use components, coming in a set for the clinician to choose from. The prevailing conditions in the oral cavity, however, differ from patient to patient. Accordingly, standard abutments have the drawbacks of not being customised.

With this in mind, prior U.S. Pat. No. 5,316,477 makes known a customisable abutment having a frusto-conical transgingival structure in which the larger end is spaced furthest from the coronal end of the fixture. The frusto-conical profile of the transgingival structure enables the mass of the transgingival structure to be reduced to create the desired profile for a specific patient.

It is an aim of the present invention to provide an improved customised dental implant and method for forming said implant.

BRIEF DESCRIPTION OF THE INVENTION

According to the present invention there is provided a method of treating a patient having a toothless site in a jaw comprising the step of:

(a) providing a fixture for anchorage in the bone of the jaw at the toothless site having a coronal end, (b) anchoring the fixture in the bone such that the coronal end is submerged beneath the coronal margin of the gingival layer at the toothless site, (c) providing an abutment which is securable in an operational position to the fixture through an opening provided through the gingival layer to the fixture, the abutment having a transgingival structure which comprises an apical section which tapers outwardly from an apical end of the transgingival structure which in the operational position of the abutment is co-planar with the coronal end of the fixture to a position at which the transgingival structure has maximum transverse dimension and a coronal section contiguous with the apical section which tapers inwardly from the maximum transverse dimension to a coronal end of the transgingival structure, the apical section terminating at the position of maximum transverse dimension with a convex outer surface profile, (d) removing material from the transgingival structure so as to form a peripheral shoulder of a profile which closely follows that of the coronal margin of the gingival layer at said opening, and (e) forming a crown structure which seats on the peripheral shoulder when the abutment is secured to the fixture.

In an embodiment of the invention the position of maximum transverse dimension is the junction of the convex outer surface profile of the apical section with the coronal section.

In an embodiment of the invention the coronal section of the transgingival structure of the abutment has a frusto-conical outer surface profile between the position of maximum transverse dimension and the coronal end. The transgingival structure may instead have a stepped outer surface profile between the position of maximum transverse dimension and the coronal end.

In an embodiment of the invention the apical section has a tulip-shape with a stem in-between the apical end and the convex outer surface profile. The stem may have a concave outer surface profile.

In an embodiment of the invention the abutment is formed from a biocompatible material, for example a metal such as titanium.

In an embodiment of the invention the maximum transverse dimension of the transgingival structure is greater than the transverse dimension of the coronal end of the fixture. In fact, the maximum transverse dimension of the transgingival structure may be greater than the maximum transverse dimension of the fixture if this is not presented by the coronal end of the fixture.

In an embodiment of the invention the abutment is screw retained to the fixture. For instance, the abutment may have a stepped screw passage through which a screw can be threaded into an internally threaded bore in the coronal end of the fixture bringing a head of the screw into abutment with the step in the screw passage thereby locking the abutment to the fixture.

In an embodiment of the invention the crown structure is cemented to the abutment. To this end, the method of the invention may further comprise the steps of applying a removable spacer to a section of the transgingival structure which extends from a position disposed coronally of the peripheral shoulder to the coronal end, building up the crown structure from the transgingival structure with the removable spacer thereon, removing the spacer so that when the crown structure seats on the peripheral shoulder of the abutment there is an annular space between the crown structure and the section of the transgingival structure for cement to be disposed for cementing the crown structure to the abutment.

In an embodiment of the invention the peripheral shoulder is so formed on the transgingival structure of the abutment that when the abutment is secured to the fixture the buccal aspect of the peripheral shoulder is disposed intragingivally and the lingual aspect is disposed supragingivally. Having the buccal aspect disposed intragingivally gives improved aesthetics whereas having the lingual aspect of the peripheral shoulder disposed supragingivally is particularly useful where the crown structure is cemented to the abutment as it enables the clinician to get sufficient purchase on the crown structure to remove it from the abutment.

In an embodiment of the invention the toothless site is a single-tooth site and the crown structure presents a single-tooth crown.

In an embodiment of the invention the toothless site is a multiple-tooth site and the method comprises the steps of anchoring a number of the fixtures in the jaw at the toothless site beneath the coronal margin of the gingival layer, providing a number of the abutments which corresponds to that of the fixtures for securement to the fixtures through openings provided through the gingival layer to each fixture, removing material from the transgingival structure of each abutment so as to form a peripheral shoulder on each abutment of profile which closely follows that of the coronal margin of the gingival layer at the opening to the associated fixture and forming the crown structure such that it bridges the abutments when secured to the fixtures and presents a range of single-tooth crowns. The crown structure in this embodiments may be a full or partial bridge or overdenture.

In an embodiment of the invention the or each abutment is selected from a set of standards abutments having different maximum transverse dimensions.

In an embodiment of the invention the or each fixture has a socket in the coronal end thereof and the or each abutment has a complementary plug structure disposed apically of the transgingival structure.

By way of example, preferred embodiments of the invention will now be described with reference to the accompanying Figures of drawings.

DESCRIPTION OF THE PREFERRED EMBODIMENTS OF THE INVENTION

Figure 1:
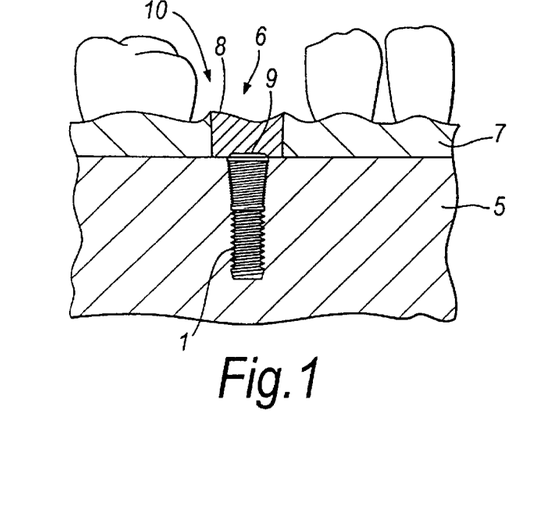
FIG. 1 is a partial cross-sectional side view of a toothless site in a jaw in need of a single-tooth replacement with a fixture having been anchored in the jaw bone beneath the coronal margin of the gingival layer.

Referring to FIG. 1, a method for replacing a lost natural tooth at a toothless site 10 in a patient's jaw in accordance with a first embodiment of the present invention firstly requires positioning a self-tapping titanium screw-type fixture 1 of circular cross-section in a bore in the jaw bone 5 at the toothless site 10. This is achieved by making an incision in the gingival layer 7 at the toothless site 10 to form a first opening 6 to the jaw bone 5, drilling the bore and then screwing the fixture 1 into the bore such that a coronal end 9 of the fixture 1 is submerged below the coronal margin 8 of the gingival layer 7. As can be seen, the coronal end 9 of the fixture is presented by a bevelled surface and ideally the fixture 1 is implanted such that the bevelled surface is disposed intragingivally, that is to say, above the margin of the jaw bone 5.

In the coronal end 9 of the fixture 1 there is a socket (not shown) having a frusto-conical entrance section, a polygonal intermediate section and a terminal internally-threaded section. After the fixture 1 has been screwed into the bore in the jaw bone 5 a healing cap (not shown) is connected thereto through the socket in the coronal end 9. The first opening 6 in the gingival layer 7 is then sutured and the fixture 1 left unloaded for a first healing period to allow the surrounding bone 5 to grow into direct contact with the fixture 1 (osseointegration) and thereby anchor it securely.

Figure 2:
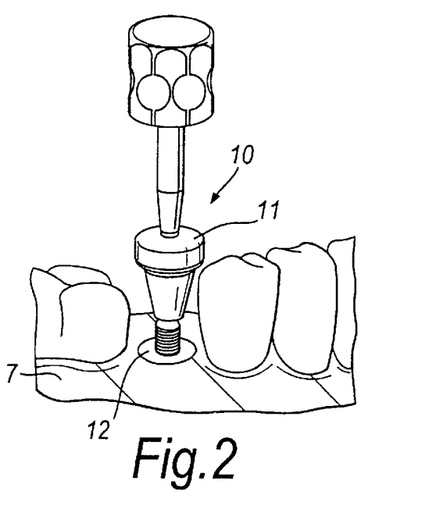
FIG. 2 shows a healing abutment in the process of being installed on the fixture after osseointegration thereof with the jaw bone.

Referring to FIG. 2, after the first healing period the section of the gingival layer 7 in the immediate vicinity of the fixture 1 (hereinafter the "peri-fixture gingival layer section") is incised again to form a second opening 12 therethrough for replacement of the healing cap with a healing abutment 11. The healing abutment 11 is left for a second healing period during which the soft tissue of the second opening 12 in the peri-fixture gingival layer section grows into contact with the healing abutment 11 so as to be shaped thereby.

Figure 3A:
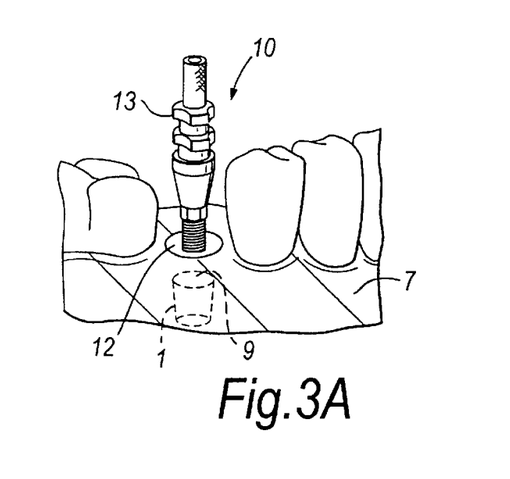
FIGS. 3A and 3B shows a pick-up transfer component in the process of being installed on the fixture in place of the healing abutment through a shaped opening formed in the peri-fixture gingival layer section by the healing abutment.
Figure 3B:
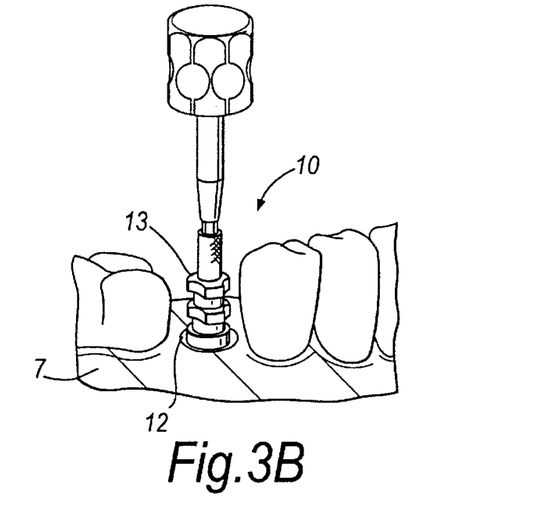
Figure 4:
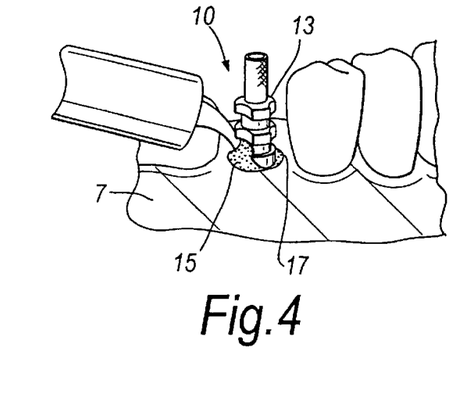
FIG. 4 shows an impression material deposited in an annular channel formed in-between the transfer component and the inner wall of the shaped opening in the peri-fixture gingival layer section.
Figure 5:
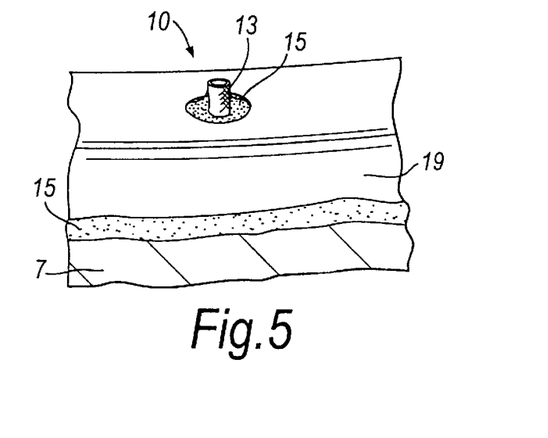
FIG. 5 shows a section of an impression tray having been pushed down on the toothless site of the jaw.

As will be understood by reference to FIGS. 3 to 5, after the second healing period the healing abutment 11 is removed and an impression is taken of the toothless site 10 with implanted fixture 1. The impression is taken by providing a pick-up transfer component or impression coping 13 which is of a maximum diameter less than that of the second opening 12 and inserting the impression coping 13 through the second opening 12 into releasable securement to the socket of the fixture 1 whereby an annular 17 space is formed between the impression coping 13 and the inner wall of the second opening 12. After the impression coping 13 has been secured to the fixture 1 an elastic impression material 15 is injected into the annular space 17 around the impression coping 13 and then a rigid impression tray 19 filled with the elastic impression material 15 is pressed down onto the toothless site 10 with the impression coping 13 protruding from the rigid impression tray 19.

Figure 6:
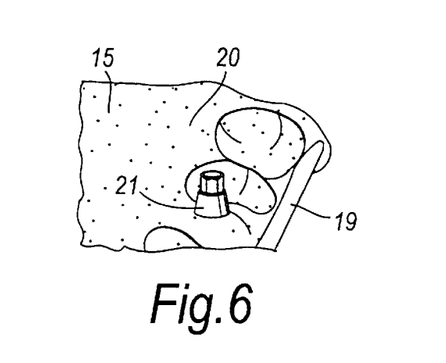
FIG. 6 shows the section of the impression tray after removal thereof from the oral cavity and turned upside down to reveal an impression pattern and protruding fixture mating end of the transfer component.
Figure 7:
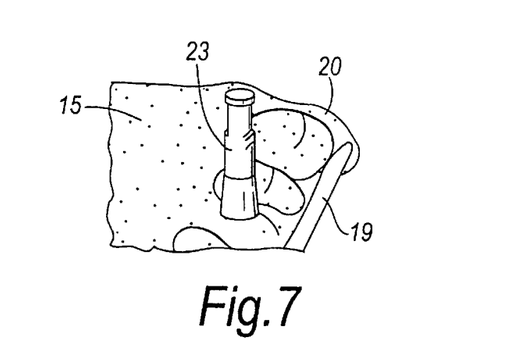
FIG. 7 is a view corresponding to FIG. 6 with a fixture analogue mounted to the fixture mating end of the transfer component.

Referring now to FIGS. 6 and 7, the impression tray 19 subsequently removed from the oral cavity and turned over to expose an impression pattern 20 of the toothless site 10 from which a fixture mating end 21 of the impression coping 13 protrudes and to which a fixture replica or analogue 23 is secured through a socket (not shown) in the fixture analogue having a frusto-conical entrance section and a polygonal intermediate or terminal section of corresponding profile and dimensions to the frusto-conical entrance section and polygonal intermediate section of the socket in the fixture 1.

Figure 8:
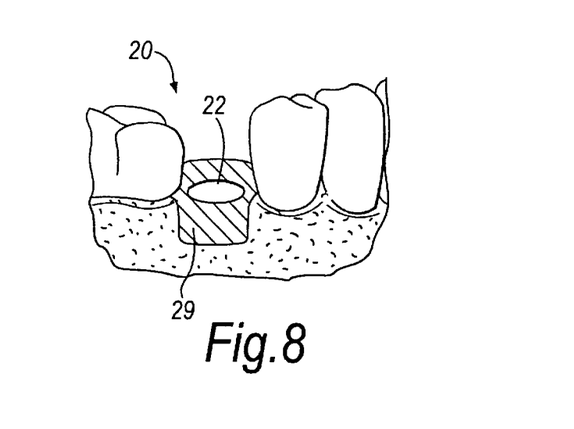
FIG. 8 is a scrap view of a model formed from the impression pattern in which the toothless site has been reproduced and which includes the fixture analogue (not shown) and a removable peri-fixture gingival layer section replica.

Referring to FIG. 8, a master cast or model 20 of the toothless site 10 containing the fixture analogue 23 (not shown) and a removable soft material replica 29 of the peri-fixture gingival layer section is fabricated from the impression pattern 20 in a manner known per se, details of which can be gathered from inter alia U.S. Pat. No. 5,674, 071. The peri-fixture gingival layer section replica 29 contains an opening 22 to the fixture analogue 23 of profile and dimensions corresponding to that of the second opening 12 in the peri-fixture gingival layer section.

Referring now to FIGS. 9 to 12, one from a set of three standard titanium abutments 31a, 31b, 31c in accordance with the present invention is selected for placement on the fixture analogue 23 in the model 20. Each abutment 31a, 31b, 31c has a fixture mating end 32 comprising a polygonal section 33 and a frusto-conical section 35 which are complementary to the polygonal and frusto-conical sections of the socket in the fixture 1 and fixture analogue 23. The complementary ploygonal cross-sections provide anti-rotation and indexing properties to the connection between the abutments 31a, 31b, 31c and the fixture 1 and fixture analogue 23.

Figure 9A:
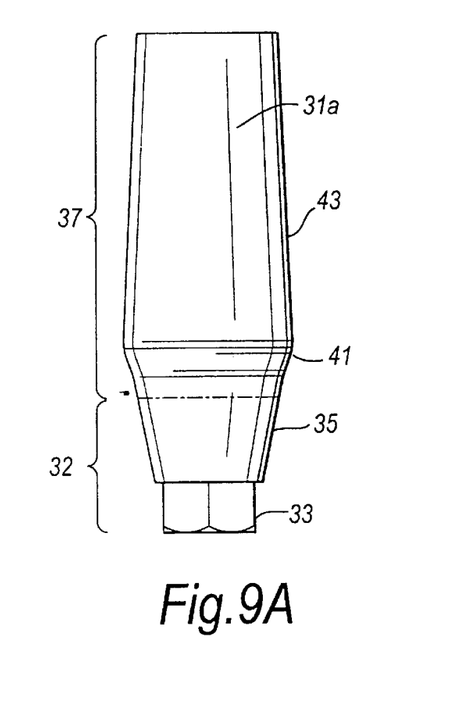
FIGS. 9A to 9C are side views of abutments in accordance with the invention.
Figure 9B:
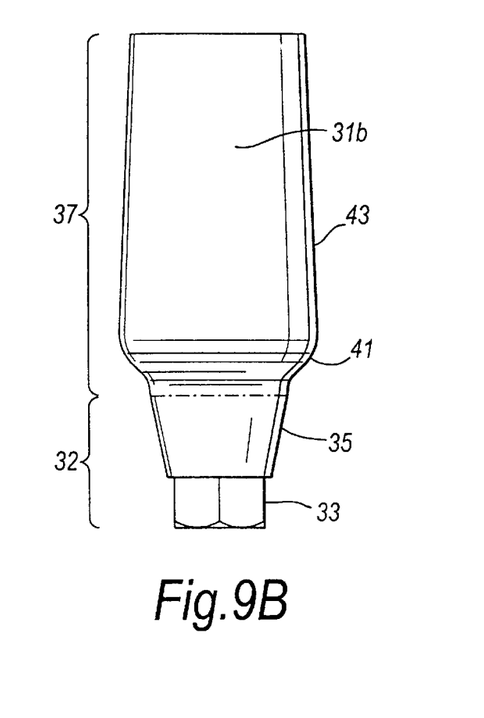
Figures 10, 11, 12, 18:
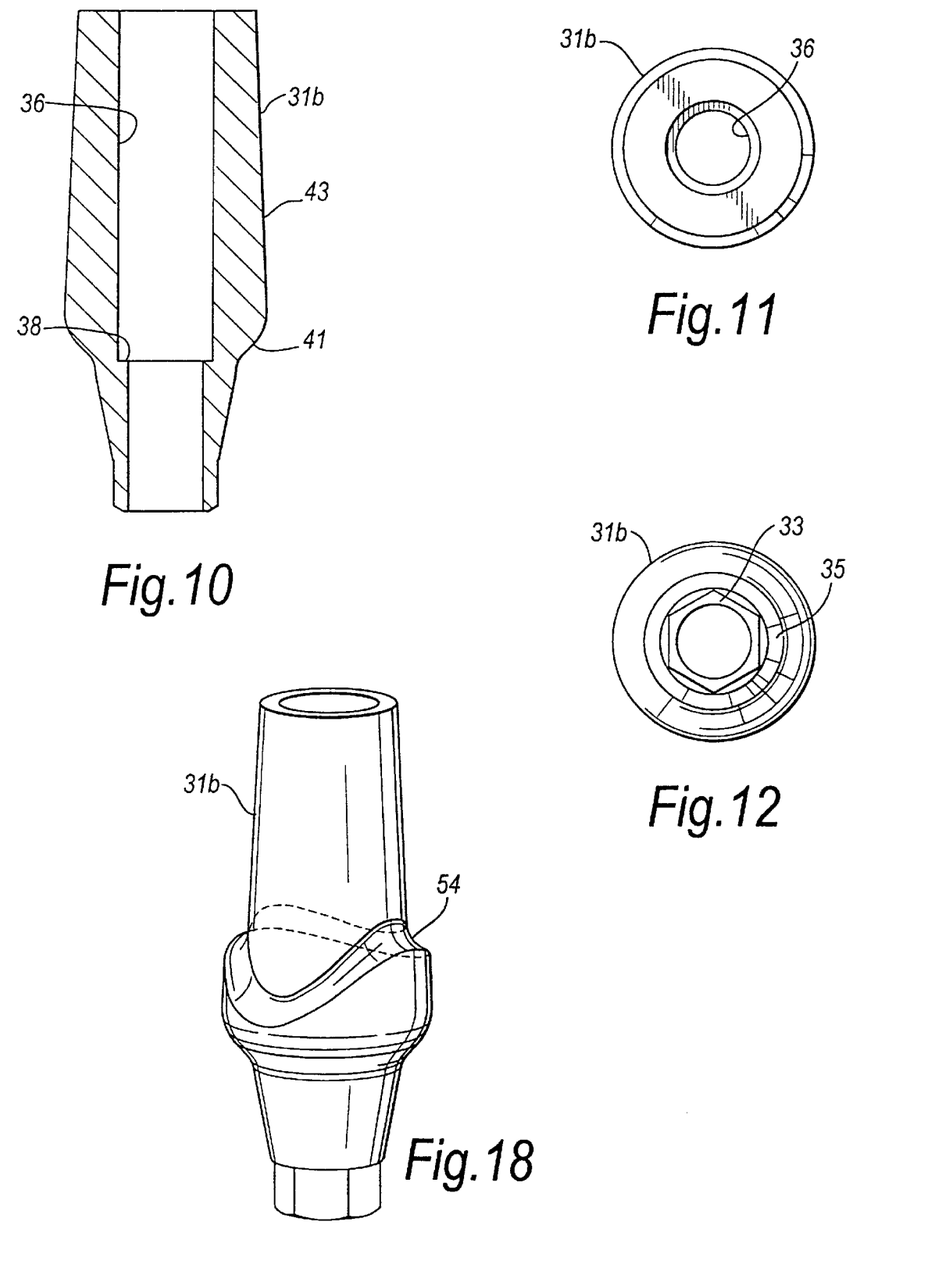
FIG. 10 is a cross-sectional side view of the abutment of FIG. 9B.
FIG. 11 is a plan view of the abutment of FIG. 9B.
FIG. 12 is an underneath plan view of the abutment of FIG. 9B.
FIG. 18 is a perspective view of the abutment with the profiled peripheral shoulder.

As illustrated by the cross-section in FIG. 10 of the abutment 31b of FIG. 9B, the abutments 31a, 31b, 31c each have an open-ended axial passage 36 which has a shoulder 38 whereby an abutment screw (not shown) is able to pass through the abutments 31a, 31b, 31c into engagement with the internally-threaded section of the socket in the fixture 1 with a head of the screw bearing on the shoulder 38 in the passage 36 so as to lock the abutments 31a, 31b, 31c to the fixture 1.

Figure 9C:
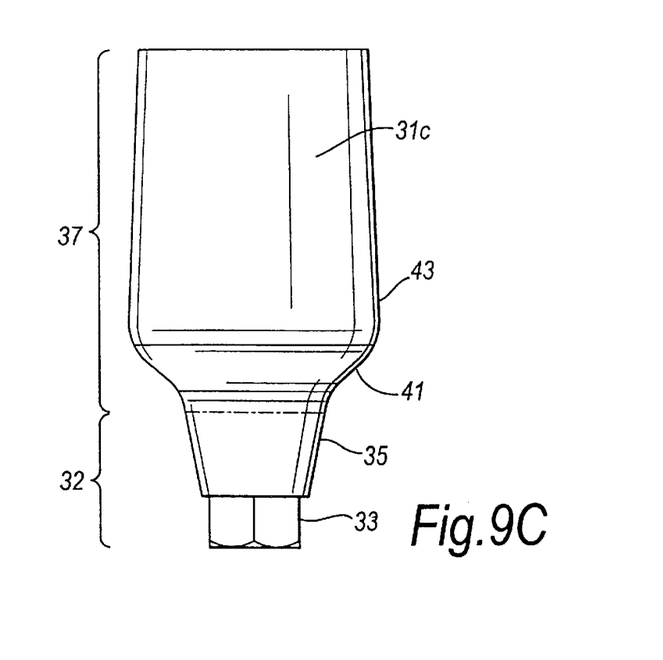

Each abutment 31a, 31b, 31c has a transgingival structure 37 which when the fixture mating end 32 seats in the socket of the fixture 1 or fixture analogue 23 extends from the coronal end of the fixture 1 or fixture analogue 23 through the gingival layer 7 or peri-fixture gingival layer section replica 29 respectively. As shown in FIGS. 9 to 10, the transgingival structure 37 of each abutment 31a, 31b, 31c is defined by a tulip-shaped apical section 41 having a concave profile stem portion and a convex profile head portion and a coronal section 43 of a frusto-conical profile with the interface of the apical and coronal sections 41, 43 defining the maximum diameter of the transgingival structure 37. The three standard abutments 31a, 31b, 31c differ from one another in that their transgingival structures 37 have different maximum diameters.

Figure 13:
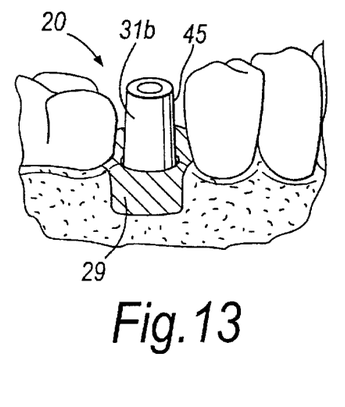
FIG. 13 is a view corresponding to FIG. 8 with the abutment of FIG. 9B mounted to the fixture analogue (not shown)

With the foregoing in mind, the abutments 31a, 31b, 31c which best fits the second opening 12 formed in the gingival layer 7 at the toothless site 10 in the jaw of the patient is selected for placement on the fixture analogue 23. FIG. 13 shows the selected abutment, in this case the abutment 31b of the FIG. 9B with the intermediate maximum diameter, placed on the fixture analogue 23 with a coronal or supragingival section 45 of the transgingival structure 37 exposed above the peri-fixture gingival layer section replica 29.

Figure 14:
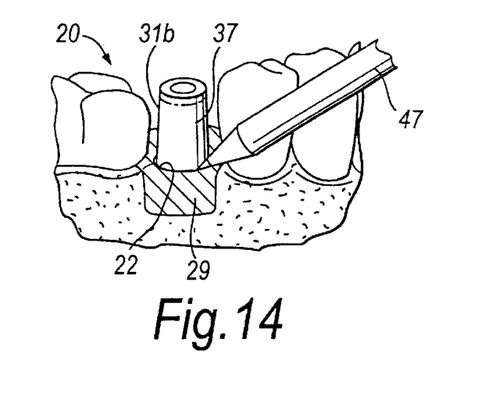
FIG. 14 is a view corresponding to FIG. 13 with a permanent marker marking on the abutment the coronal margin of the peri-fixture gingival layer section replica and the height needed.
Figure 15:
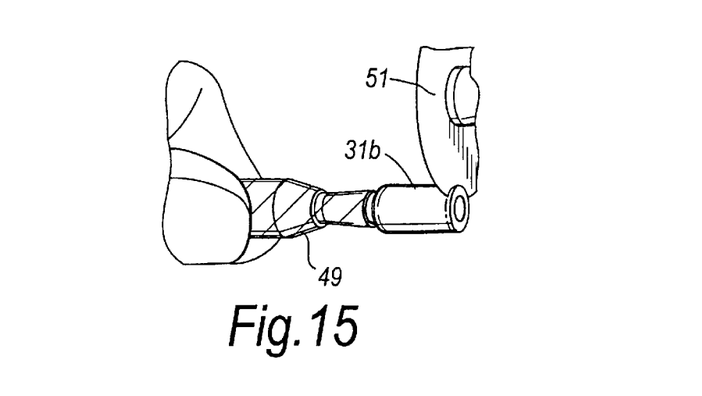
FIG. 15 shows the abutment mounted in a grinding handle and a cutting disc cutting off the surplus coronal portion of the abutment.

Turning now to FIG. 14, the coronal margin of the peri-fixture gingival layer section replica 29 at the opening 22 therein is marked on the abutments 31b with a fine tip permanent marker 47 together with markings for the vertical dimension and mesial-distal width required for the abutment 31b to satisfy the clinical situation at the toothless site 10, e.g. taking account of any non-parallelism of the fixture axis with the axis of the adjacent teeth. The abutment 31b is then unseated from the fixture analogue 23 and, as shown in FIG. 15, mounted in a grinding handle 49 for the vertical dimension to be reduced with a cutting disc 51.

Figure 16:
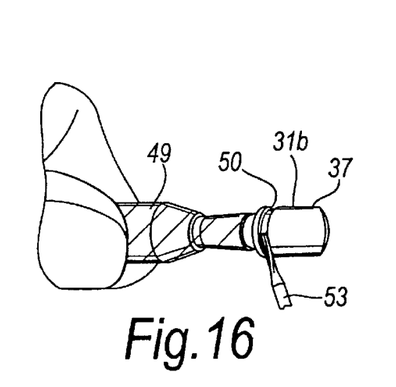
FIG. 16 shows the abutment in the grinding handle being machined with a burr to form a recess of profile closely following that of the marking made of the coronal margin of the peri-fixture gingival layer section replica.
Figure 17:
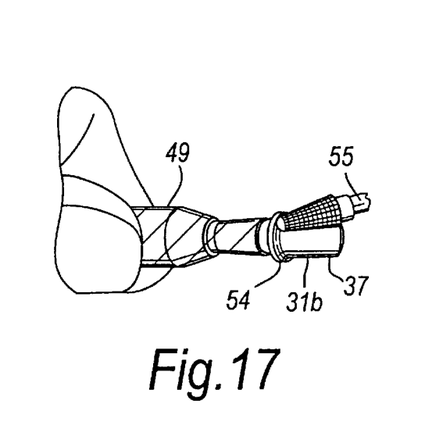
FIG. 17 shows the abutment in the grinding handle being machined with a cutter to reduce the transverse dimension of the abutment above the recess to form a profiled peripheral shoulder.

Referring to FIGS. 16 and 17, a recess 50 of profile closely following that of the marking made for the coronal margin of the peri-fixture gingival layer section replica 29 is made with a high-speed (e.g. 200,000 rpm), cross-cut, round-ended, fissure carbide burr 53, for example Jet™ No. 1958 (KERR Inc). The width of the transgingival structure 37 above the recess 50 is then reduced with a titanium cutter 55 in a 15–30,000 rpm hand-piece to turn the recess 50 into a shoulder preparation 54 which, as is more clearly shown in FIG. 18, has a wave profile which mimics that of the coronal margin of the peri-fixture gingival layer section replica 29 at the opening 22 and hence the coronal margin 8 of the peri-fixture gingival layer section at the second opening 12 in the toothless site 10. Although the profile of the shoulder 54 mimics that of the coronal margin 8 of the peri-fixture gingival layer section at the second opening 12 in the toothless site 10, it is prepared such that when the abutment 31b is secured to the fixture 1 at the toothless site 10 the buccal aspect of the shoulder 54 will be disposed apically of the coronal margin 8 and the lingual aspect will be disposed coronally of the coronal margin 8, as will be discussed in more detail hereinafter.

The abutment 31b so prepared is placed back in the model 20 and checked for design and occlusal clearance. After any further necessary machining, the portion of the transgingival structure 37 disposed coronally of the shoulder preparation 54 is painted to a thickness of approximately 50 μm with a cement spacer, preferably making sure that at least a 1 mm distance is kept from the shoulder preparation 54 itself.

Figure 19:
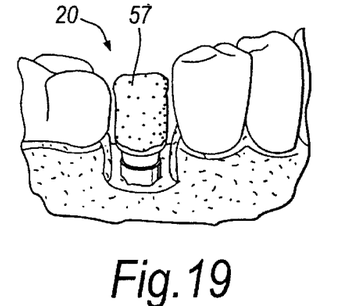
FIG. 19 shows the prepared abutment remounted on the fixture analogue in the model with a wax pattern applied thereto.
Figure 20:
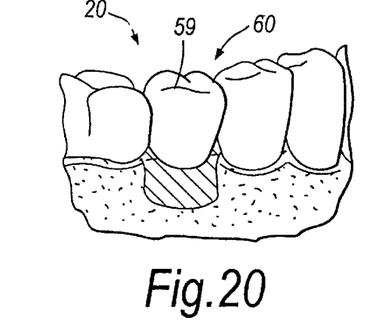
FIG. 20 shows a single-tooth crown formed from the wax pattern releasably mounted on the abutment on the model.

As shown in FIGS. 19 and 20, a wax pattern 57 is then built-up directly on the shoulder 54 and checked on the model 20. After making any shape changes needed, the wax pattern 57 is converted to a metallic core, e.g. of gold, by lost-wax casting in a manner known per se, details of which can be gathered from inter alia U.S. Pat. No. 4,744,753. A porcelain layer 59 is then fused to the metallic core by firing to form a single-tooth crown 60. As will appreciated by those versed in the art, the crown 60 may be built-up differently to yield an all ceramic crown, all metallic crown or various other composite crown constructions.

At this stage in the manufacturing process, the cement spacer is blasted off the transgingival structure 37 of the abutment 31b, for instance with aluminium oxide having a grit size of approximately 50 μm, preferably taking care to stay at least 1 mm away from the shoulder preparation 54 when the cement spacer has been kept that distance from the shoulder preparation 54. An annular space will thus exist between the portion of the transgingival structure disposed coronally of the shoulder 54 and the crown 60 when the crown 60 is seated on the shoulder 54 into which cement is able to be applied for cementing the crown 60 to the abutment 31b.

Figure 21:
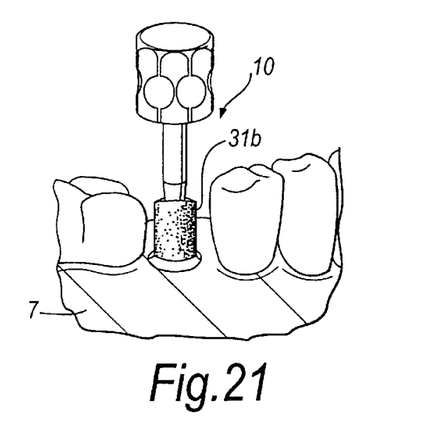
FIG. 21 shows the abutment in the process of being screw retained to the fixture in the jaw bone at the toothless site in the jaw.
Figure 22:
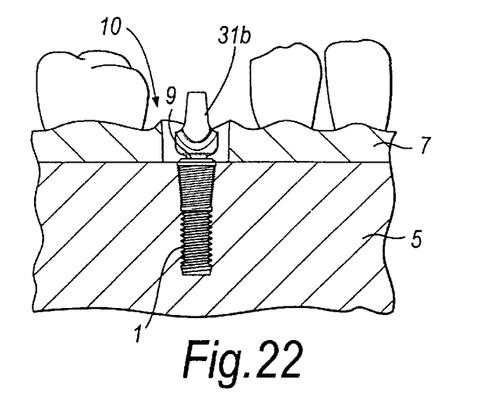
FIG. 22 is a side view, partly in cross-section, of the abutment screw retained to the fixture in the jaw.
Figure 23:
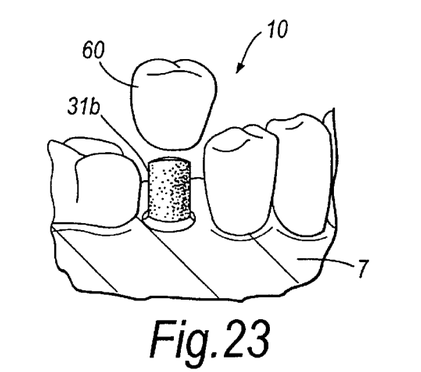
FIG. 23 shows the single-tooth crown in the process of being mounted on the abutment screw retained to the fixture in the jaw.
Figure 24:
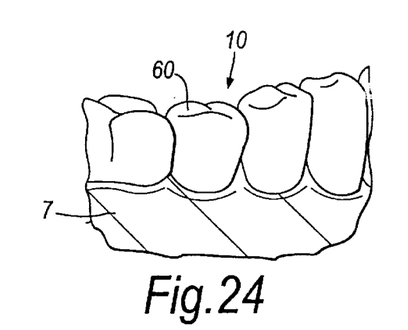
FIG. 24 shows the single-tooth crown in the jaw after cementation thereof to the abutment.

With this in mind, FIG. 21 shows the abutment 31b being screw retained to the fixture 1 (not shown) at the toothless site 10. FIG. 22 shows the emergence profile of the transgingival structure 37 of the abutment 31b from the coronal end 9 of the fixture 1 when the abutment 31b is secured to the fixture 1. As can be seen, the transgingival structure 31b emerges centrally from the coronal end 9 and has a diameter at its apical end which is less than that of the bevelled surface at the coronal end 9 of the fixture 1. As shown in FIGS. 23 and 24, after the abutment 31b is secured to the fixture 1 the crown 60 is cemented in place on the shoulder 54 of the abutment 31b by a temporary cement such as Temp-Bond™ (Kerr Inc.) or a permanent cement such as a phosphate or glass-ionomer cement.

It will be appreciated that forming the shoulder 54 such that the buccal aspect thereof is disposed apically of the coronal margin 8 of the gingival layer 7 at the second opening 12 when the abutment 31b is screw retained to the fixture 1 results in the crown 60 being submerged beneath the coronal margin 8 when cemented to the abutment 31b. This ensures that the toothless site 10 has a natural tooth appearance beneath the coronal margin 8 of the gingival layer 7. With regard to forming to the lingual aspect of the shoulder 54 such that is disposed coronally of the coronal margin 8 of the gingival layer 7 at the second opening 12, this gives the clinician leverage on the crown 60 if the crown 60 is required to be disconnected from the abutment 31b.

The abutments 31a, 31b, 31c described hereinabove can be modified so as not to include the polygonal section 33 at the fixture mating end 32. Such modified abutments could sill be used in the fixture 1 and fixture analogue 23. Alternately, a further fixture and fixture analogue could be used in which the polygonal sections in the sockets thereof are also omitted.

A method for replacing a plurality of lost natural tooth in accordance with a second embodiment of the present invention will now be described. In this embodiment of toothless site in the jaw is a gap where several juxtaposed natural teeth have been lost. Many of the steps in the method according to the second embodiment are the same as those used in the method of the first embodiment described hereinabove with reference to FIGS. 1 to 24 and therefore, since they will be understood by reference to the Figures of drawings used for illustrating the first embodiment, will only be described in brief.

Figure 25:
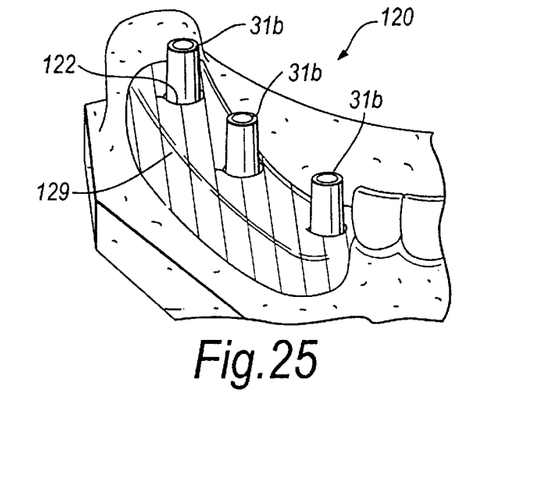
FIG. 25 is a scrap view of a model formed of a toothless site in a jaw in need of a multi-crown structure with a plurality of the abutments of FIG. 9B mounted on the model on fixture analogues (not shown) submerged beneath a peri-fixture gingival layer section replica.

Firstly, two or more fixtures are implanted in the toothless site and the first healing period a healing abutment is placed on each fixture through a second opening thereto for the second healing period. As shown in FIG. 25, a model 120 of the toothless site which contains a fixture analogue for each fixture and a removable soft tissue replica 129 of the peri-fixture gingival layer section in which there are formed openings 122 corresponding to the second openings at the toothless site is then fabricated by releasably securing a pick-up impression coping to each fixture through the second openings and impression taking a rigid impression tray.

One of the abutments 31a, 31b, 31c of FIG. 9 is then selected for each fixture analogue in the model 120 depending on the prevailing conditions at each fixture site. For simplicities sake, it is assumed hereinafter that the abutment 31b of FIG. 9B with the transgingival structure 37 of intermediate maximum diameter is selected for use for each fixture analogue. As shown in FIG. 25, the selected abutments 31b are installed on the fixture analogues in the model 120 whereupon the transgingival structure 37 of each abutment 31b is marked with the coronal margin of the peri-fixture gingival layer section replica 29 at the opening 122 to the associated fixture analogue as well as with the correct vertical dimension and mesial-distal width.

The abutments 31b are then disconnected from the associated fixture analogue and mounted successively in a grinding handle for the vertical dimension to be reduced with a cutting disc and a shoulder preparation to be formed with a burr and cutter. The transgingival structure 37 of each abutment 31b is then painted to a thickness of approximately 50 μm with a cement spacer, preferably making sure that at least a 1 mm distance is kept from the shoulder preparation.

Figure 26:
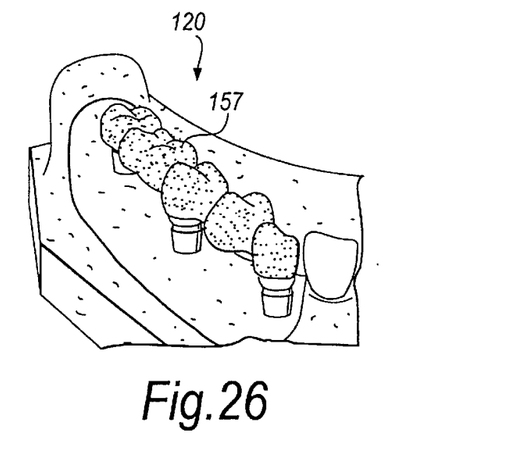
FIG. 26 shows the model of FIG. 25 with the abutments post-shoulder preparation supporting a bridging wax pattern.
Figure 27:
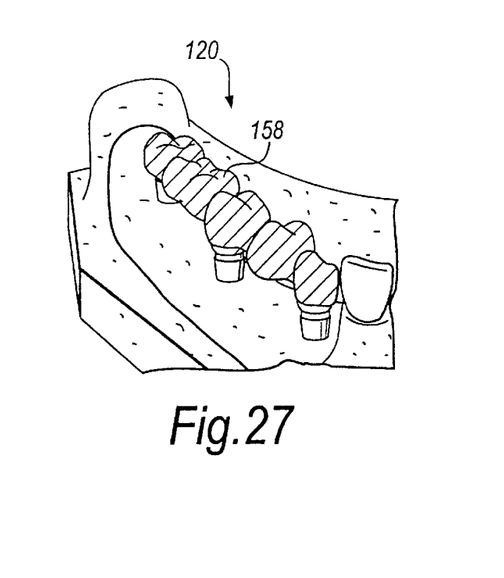
FIG. 27 is a view corresponding to FIG. 26 with the wax pattern having been converted to a metallic casting by lost-wax casting.
Figure 28:
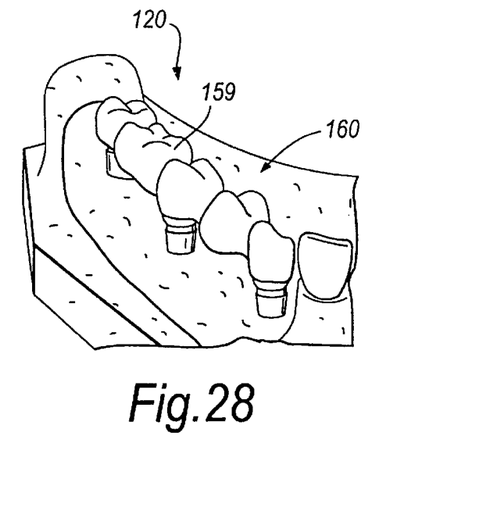
FIG. 28 is a view corresponding to FIG. 27 with a porcelain layer having been fused to the metallic casting by firing to form the multi-crown structure.

As shown in FIG. 26, the abutments 31b are replaced in the model 120 and a wax pattern 157 which bridges the abutments 31b built-up directly from the shoulder preparations. As will be understood by reference to FIGS. 27 and 28, the wax pattern 157 is converted to a metallic core 158 by lost-wax casting and a porcelain layer 159 then fused to the metallic core 158 by firing to form a multi-tooth crown structure or partial bridge 160.

Figure 29:
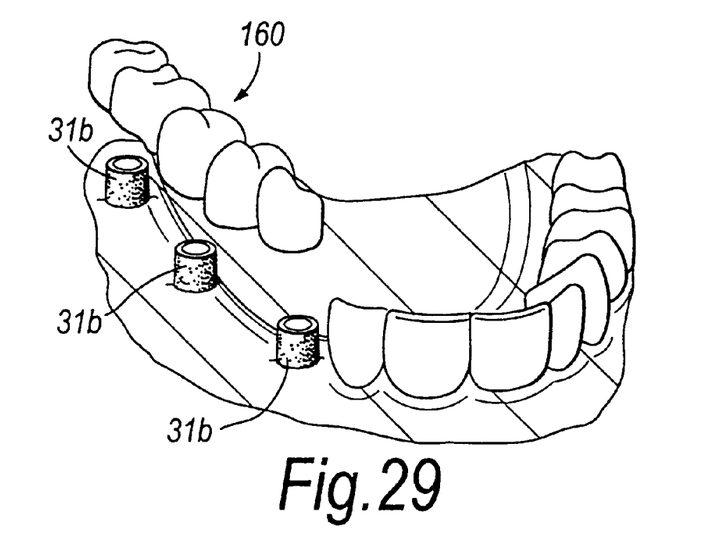
FIG. 29 shows the multi-crown structure in the process of being mounted on the abutments after they have been screw retained to associated fixtures anchored in the jaw bone at the toothless site.
Figure 30:
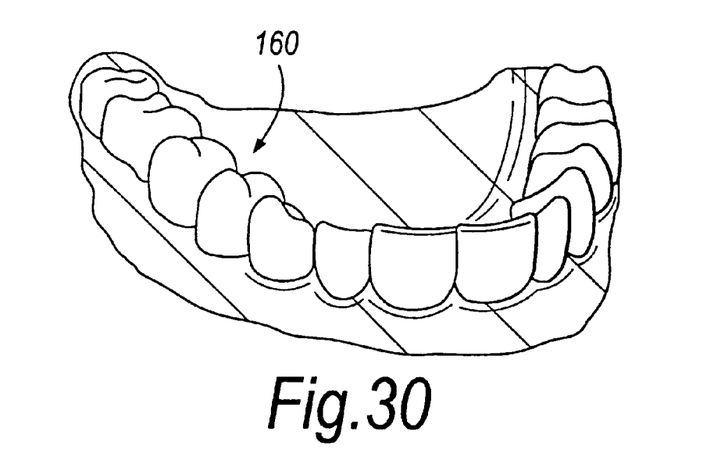
FIG. 30 shows the multi-crown structure in the jaw after cementation to the abutments.

The partial bridge 160 is removed from the model 120 and the cement spacer then blasted off each abutment 31b, preferably taking care to stay at least 1 mm away from the shoulder preparations when the cement spacer has been kept that distance from the shoulder preparations. As will be understood from FIGS. 29 and 30, the abutments 31b are then screw retained to the fixtures in the jaw bone at the toothless site and the partial bridge 160 cemented in place on the shoulder preparations of the abutments 31b using a temporary cement such as Temp-Bond ™(KERR Inc.) or a permanent cement such as a phosphate or glass-ionomer cement.

It will be readily appreciated by the skilled worker in the art that the method according to the second embodiment of the present invention can be extrapolated for the case where all of the teeth in one of the jaws have been lost (full edentulousness) and need replacing with a full bridge. Moreover, a multi-crown structure could be seated on a single fixture-abutment assembly, e.g. if the multi-crown structure only presents a pair of single-tooth crowns.

Finally, it will be understood that the invention has been described in relation to preferred embodiments and can be modified in many different ways within the scope defined by the appended claims.

What is claimed is:

1. A method of forming a customized dental abutment which is capable of being secured to a dental fixture anchored in the bone of a jaw of a patient at a toothless site through an opening being provided through the gingival layer of the patient, comprising the steps of:

providing the fixture for anchorage in the bone of the jaw of the patient wherein the fixture has a coronal end;

anchoring the fixture in the bone such that the coronal end is submerged beneath the coronal margin of the gingival layer at the toothless site;

providing a customizable abutment to the fixture or an analogue of the fixture and gingival layer;

marking the coronal margin of the gingival layer at the opening on the customizable abutment; and removing material from the customizable abutment to form a peripheral shoulder of a profile which closely follows that of the coronal margin of the gingival layer at the opening to form the customized dental abutment.

2. The method according to claim 1, wherein the abutment has a transgingival structure which comprises an apical section with tapers outwardly from an apical end of the transgingival structure which in the operational position of the abutment is co-planar with the coronal end of the fixture to a position at which the transgingival structure has a maximum transverse dimension and a coronal section contiguous with the apical section which tapers inwardly from the maximum transverse dimension to a coronal end of the transgingival structure, the apical section terminating at the position of maximum transverse dimension with a convex outer surface profile, and material is removed from the transgingival structure to form the peripheral shoulder, and wherein the method further comprises the step of forming a crown structure which sits on the peripheral shoulder when the abutment is secured to the fixture.

3. The method according to claim 2, wherein the coronal section of the transgingival structure of the abutment has a frusto-conical outer surface profile between the position of maximum transverse dimension and the coronal end.

4. The method of according to claim 2, wherein the apical section of the transgingival structure of the abutment has a tulip-shape with a stem in-between the apical end and the convex outer surface profile.

5. The method according to claim 4, wherein the stem has a concave outer surface profile.

6. The method according to any one of claims 2–5, wherein the maximum transverse dimension of the transgingival structure is greater than the transverse dimension of the coronal end of the fixture.

7. The method according to claim 6 wherein the crown structure is cemented to the abutment and the method further comprises the step of:

applying a removable spacer to a section of the transgingival structure which extends from a position disposed coronally of the peripheral structure to the coronal end;

building up the crown structure from the transgingival structure with the removable spacer thereon; and removing the spacer so that when the crown structure seats on the peripheral shoulder of the abutment there is an annular space between the crown structure and the section of the transgingival structure for cement to be disposed for cementing the crown structure to the abutment.

8. The method according to any one of claims 2–5, wherein the crown structure is cemented to the abutment and the method further comprises the steps of:

applying a removable spacer to a section of the transgingival structure which extends from a position disposed coronally of the peripheral shoulder to the coronal end;

building up the crown structure from the transgingival structure with the removable spacer thereon; and removing the spacer so that when the crown structure seats on the peripheral shoulder of the abutment there is an annular space between the crown structure and the section of the transgingival structure for cement to be disposed for cementing the crown structure to the abutment.

9. The method according to any one of claims 2–5, wherein the toothless site is a single-tooth site and the crown structure presents a single-tooth crown.

10. The method according to claim 2, wherein the toothless site is multiple-tooth site and the method further comprises the steps of anchoring a number of the fixtures in the jaw at the toothless site beneath the coronal margin of the gingival layer, providing a number of the customizable dental abutments which corresponds to that of the fixtures for securement to the fixtures through openings provided through the gingival layer to each fixture, removing material from the transgingival structure of each abutment so as to form a peripheral shoulder of each abutment with a profile which closely follows that of the coronal margin of the gingival layer at the opening to the associated fixture and forming the crown structures such that the crown structures bridge the abutments when secured to the fixtures and presents a range of single-tooth crowns.

11. The according to claim 2 or 10, wherein the or each customizable abutment is selected from a set of customizable abutments having different maximum transverse dimensions.

12. A customized dental abutment prepared from a customizable dental abutment in accordance with the method of claim 1.

13. The customized dental according to claim 12, wherein the dental abutment has a transgingival structure comprising:

an apical section which tapers outwardly from an apical end of the transgingival structure to a position at which the transgingival structure has a maximum transverse dimension, and a coronal section contiguous with the apical section with tapers inwardly from the maximum transverse dimension to a coronal end of the transgingival structure, and wherein the apical section terminates at the position of maximum transverse dimension with a convex outer surface profile, and material is removed from the transgingival structure to form the peripheral shoulder.

14. The customized dental abutment according to claim 13, wherein the coronal section of the transgingival structure of the abutment has a frusto-conical outer surface profile between the position of maximum transverse dimension and the coronal end.

15. The customized dental abutment according to claim 13, wherein the apical section of the transgingival section of the abutment has tulip-shape with a stem in-between apical end and the convex outer surface profile.

16. The customized dental abutment according to claim 15, wherein the stem has a concave outer surface profile.

17. The customized dental abutment according to any one of claims 13, 14, 15 or 16, wherein the maximum transverse dimension of the transgingival structure is greater than the transverse dimension of the coronal end of the fixture.

18. The customized dental abutment according to the claim 12, 13 or 14, wherein the abutment has an open ended axial passage wherein an abutment screw for securing the abutment to the dental implant is able to pass through the abutment into engagement with the dental implant.

19. The customized dental abutment according to claim 12, 13 or 14, wherein each abutment has a dental implant mating end comprising a polygonal section and a frusto-conical section which are complementary to the shape of the dental implant.

* * * * *

UNITED STATES PATENT AND TRADEMARK OFFICE
CERTIFICATE OF CORRECTION

PATENT NO. : 6,280,195 B1
DATED : August 28, 2001
INVENTOR(S) : Broberg et al.

It is certified that error appears in the above-identified patent and that said Letters Patent is hereby corrected as shown below:

Column 9,
Line 52, "the method of according to" should read -- the method according to --.
Line 64, "step" should read -- steps --.

Column 10,
Line 28, "site is multiple-tooth site" should read -- site is a multiple-tooth site --.
Line 42, "the according to" should read -- the method according to --.
Line 55, "section with" should read -- section which --.

Column 11,
Line 3, "has tulip-shape" should read -- has a tulip-shaped -- and -- the -- should appear between the words "in-between" and "apical".

Signed and Sealed this

Eleventh Day of June, 2002

Attest:

JAMES E. ROGAN
*Attesting Officer*  *Director of the United States Patent and Trademark Office*